United States Patent

Falb et al.

[11] Patent Number: 5,560,584
[45] Date of Patent: Oct. 1, 1996

[54] SAFETY FILLING DEVICE WITH A CLOSING ELEMENT

[75] Inventors: Wolfgang Falb, Krummesse; Dirk-Stefan Reichert, Lübeck; Ernst-Günter Scharmer, Krummesse; Günther Hahmann, Lübeck, all of Germany

[73] Assignee: Drägerwerk AG, Lübeck, Germany

[21] Appl. No.: 302,045

[22] Filed: Sep. 7, 1994

[30] Foreign Application Priority Data

Sep. 13, 1993 [DE] Germany ............................ 43 31 035.4

[51] Int. Cl.⁶ .................................................. A61M 16/18
[52] U.S. Cl. .................................... 251/89.5; 128/200.14; 137/625.19
[58] Field of Search ........................ 137/614.06, 625.19; 251/89.5, 149.9; 128/200.14

[56] References Cited

U.S. PATENT DOCUMENTS

| | | | |
|---|---|---|---|
| 3,295,553 | 1/1967 | Garrett et al. | 137/614.06 |
| 4,426,063 | 1/1984 | Bormioli | 251/89.5 X |
| 4,932,398 | 6/1990 | Lancaster et al. | 251/149.9 X |
| 4,982,743 | 1/1991 | Green et al. | 128/200.14 |
| 5,149,053 | 9/1992 | Galli | 251/149.9 |

FOREIGN PATENT DOCUMENTS

| | | |
|---|---|---|
| 4106906A1 | 9/1992 | Germany . |
| 4106756A1 | 9/1992 | Germany . |
| 4108383A1 | 9/1992 | Germany . |

*Primary Examiner*—Stephen M. Hepperle
*Attorney, Agent, or Firm*—McGlew and Tuttle, P.C.

[57] ABSTRACT

A safety filling device for filling a liquid anesthetic into a filling space of an anesthetic evaporator from a storage container by means of a filling adapter, which can be pushed into an insertion opening, with a closing element, which interrupts the flow of liquid anesthetic in a switched-off position, and with a control element, which is movable in a stationary housing and sets the states of switching. A preferential position is set on the closing element during the introduction of the filling adapter into the insertion opening. A follower blocking the switched-off position is provided on the closing element between the housing and the control element, and a coding part, which engages the follower in a manner eliminating the blocking of the closing element in the operating position of the filling adapter, is provided on the filling adapter.

11 Claims, 9 Drawing Sheets

5,560,584

SAFETY FILLING DEVICE WITH A CLOSING ELEMENT

FIELD OF THE INVENTION

The present invention pertains to a safety device for filling liquid anesthetic into a filling space of an anesthetic evaporator from a storage container by means of a filling adapter, which can be pushed into an insertion opening with a filling channel for delivery of the liquid anesthetic and with a ventilation channel to compensate the filling volume in the storage container, which changes during filling, such that the ventilation channel and the filling channel are continued in the filling adapter in the operating position of the filling adapter, and with a closing element, which interrupts the flow of liquid anesthetic in a switched-off position, with a control element which is movable in a stationary housing and sets the switching states.

BACKGROUND OF THE INVENTION

A safety filling device of this class has become known from DE-A 41 06 906. The prior-art safety filling device is arranged in the area of the filling space of the anesthetic evaporator and is used to fill in a liquid anesthetic from a storage container. To do so, the end cap of a flexible, coaxial line section, which has a filling channel for filling in the liquid anesthetic and a ventilation channel for compensating the filling volume in the storage container, which changes during filling or emptying, is screwed onto the neck of the storage container. The other end of the line section is provided with a filling adapter for fastening to an insertion opening of the safety filling device. A filling channel and a ventilation channel are also located at the insertion opening. A storage container with a flexible line section screwed onto it for filling an anesthetic evaporator is shown in, e.g., FIG. 2 of DE-A 41 06 756. Before the filling adapter is pushed into the insertion opening, a closing slide, which shuts off the device-side filling channel and the ventilation channel within the insertion opening, is first removed, after which the filling adapter is pushed in, and the filling channels and the ventilation channels are brought into alignment in the operating position. A closing element in the form of a button performing stroke movements with a shut-off valve is located in the device-side filling channel, and the said shut-off valve is switched into the switched-off position prior to filling, so that no liquid anesthetic feed is possible. For filling, the storage container is turned upside down, and the shut-off valve is then opened by pulling the button, as a result of which liquid anesthetic will flow into the filling space of the anesthetic evaporator via the filling channel as a consequence of the force of gravity, while gas flows from the filling space into the storage container via the ventilation channel to compensate the decreasing filling volume in the storage container. After filling, the storage container is lowered, the shut-off valve is closed, and the filling adapter is pulled out of the insertion opening of the safety filling device. The insertion opening is then closed with the closing slide.

It is disadvantageous in the prior-art safety filling device that blocking of filling is possible when the shut-off valve is not in the switched-off position, but is open when the filling adapter is being pushed in. In this case, the filling channel of the flexible line section between the filling adapter and the storage container can be filled completely with liquid anesthetic when the storage container is swung into the upside down position, so that the exchange of liquid between the filling space and the storage container is blocked by air bubbles in the filling channel of the flexible line section, because the shut-off valve is used to initially shut off the device-side filling channel until the filling channel of the flexible line section has been completely filled with liquid anesthetic without liquid anesthetic penetrating into the ventilation channel, after the storage container has been swung into the upside down position. The filling process is then initiated by opening the shut-off valve.

An anesthetic evaporator with a safety filling device, in which a blocking device is provided between a shut-off valve acting as a closing element in the filling channel and a metering member, with which the desired concentration value is set, and with which filling is possible only when the metering member has been switched into the shut-off position, has become known from DE-A 41 08 383.

Even though the prior-art blocking device ensures that the shut-off valve can be actuated only in the switched-off position of the metering member, this does not yet ensure that the shut-off valve will also be located in the closed position when the filling adapter is pushed in, because the switching off of the metering member and filling do not necessarily need to coincide in time. It is therefore possible, e.g., that even though the metering member of the anesthetic evaporator is switched into the closed position after the use of the device in an inhalation anesthesia apparatus equipped with an anesthetic evaporator, filling will be performed only later, e.g., before the next use of the apparatus. It is not guaranteed in this case that the shut-off valve will then still be in the switched-off position.

SUMMARY AND OBJECTS OF THE INVENTION

The primary object of the present invention is to improve a safety filling device of the type described such that when the filling adapter is introduced into the insertion opening of the safety filling device, a preferred position is set on the closing element.

This object is attained by providing a follower blocking the switched-off position on the closing element between the housing and the control element and by providing—on the filling adapter—a coding part, which engages the follower in a manner eliminating the blocking of the closing element in the operating position of the filling adapter.

The advantage of the present invention is essentially the fact that the closing element can be actuated from the switched-off position only when the filling adapter has been pushed completely into the insertion opening, and the filling and ventilation channels in the filling adapter and in the insertion opening have thus also been aligned, so that an exchange of liquid anesthetic between the storage container and the filling space of the anesthetic evaporator can be initiated. By eliminating the blocking of the closing element by the filling adapter, it is achieved that actuation of the closing element from the switched-off position is possible only with the filling adapter pushed in, so that the filling channel of the flexible line section can first be filled completely with liquid anesthetic while the storage container is being swung into the upside down position, before the closing element is opened from the switched-off position and the exchange of liquid anesthetic between the storage container and the filling space is initiated as a result.

After the closing element has been closed at the end of the filling process, and the filling adapter has been removed from the insertion opening, the closing element is blocked by the follower in the switched-off position, so that an inadvertent adjustment of the closing element during the operation of the anesthetic evaporator is not possible. The closing element is preferably arranged in the device-side filling channel of the safety filling device. However, since feed of liquid anesthetic between the filling space and the storage container is possible only when both the filling channel and the ventilation channel communicate with one another, the closing element may also be arranged in the ventilation channel, or the closing element is located in both the filling channel and the ventilation channel.

The follower advantageously consists of a guide hole in the control element, a stop hole extending toward the coding part in the housing, and of a locking pin displaceable in the guide hole and/or stop hole. In the switched-off position of the closing element, the guide hole and the stop hole meet aligned at a boundary line, the locking pin covers the boundary line, and the closing element, i.e., the control element, is blocked in relation to the housing as a result. The locking pin can be displaced by the coding part up to the boundary line, so that blocking is eliminated and the control element of the closing element can be actuated. A plurality of locking pins, which are displaced by a coding part of a corresponding design up to the boundary line, may be present as well. For example, an anesthetic-specific coding is thus possible.

In an advantageous alternative embodiment of the follower, the guide hole is provided as a first guide hole in the stationary housing of the closing element, and a first stop hole is provided in the control element such that the stop hole extends toward the coding part of the filling adapter, and the first guide hole and the first stop hole pass over into each other at a boundary line in the switched-off position of the closing element, and a spring-tensioned first locking pin located in the first guide hole engages the first stop hole, thus blocking the control element in the housing. By introducing the filling adapter provided with a coding part, the first locking pin is displaced into the first guide hole at least to the boundary line, so that blocking is eliminated, and the control element can be actuated.

The coding part is advantageously designed as a projection, and the insertion opening has a coding groove, into which the projection can be pushed. It is achieved by this coding that only a filling adapter with a projection fitting the coding groove can be pushed into the insertion opening.

The control element advantageously has a pushbutton with a coding disk, and the coding disk has a recess corresponding to the coding groove, and the said recess lies congruently on the coding groove in the switched-off position of the closing element. The filling adapter can thus be pushed into the insertion opening in the switched-off position of the closing element, but it is blocked in the insertion opening when the pushbutton is turned into the switched-on position of the closing element, and the recess leaves the area in which it overlaps the coding groove.

In another advantageous embodiment, the coding part is designed as a depression in a first filling adapter, and a first transmission pin, which extends into the insertion opening and scans the depression of the first filling adapter when the latter is or has been pushed into the insertion opening, is provided between the locking pin and the first filling adapter. An anesthetic-specific coding can be achieved due to the geometry of the depression and of the first transmission pin, so that the anesthetic evaporator can be filled only with the corresponding liquid anesthetic.

The depression is advantageously stepped, and it is provided with a step which is in contact with the first transmission pin, so that the filling adapter is blocked by the step within the insertion opening when the closing element is switched from the switched-off position into the open position. When viewed from the flexible line section, the step is located behind the first transmission pin.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a detail A from FIG. 2, but with the filling adapter pushed in;

FIG. 6 is a sectional view showing the follower according to FIG. 5, but with the filling adapter pushed in;

FIG. 8 is a sectional view showing the follower according to FIG. 7, but with the filling adapter pushed in.

DETAILED DESCRIPTION OF THE PREFERRED EMBODIMENT

Figure 1:
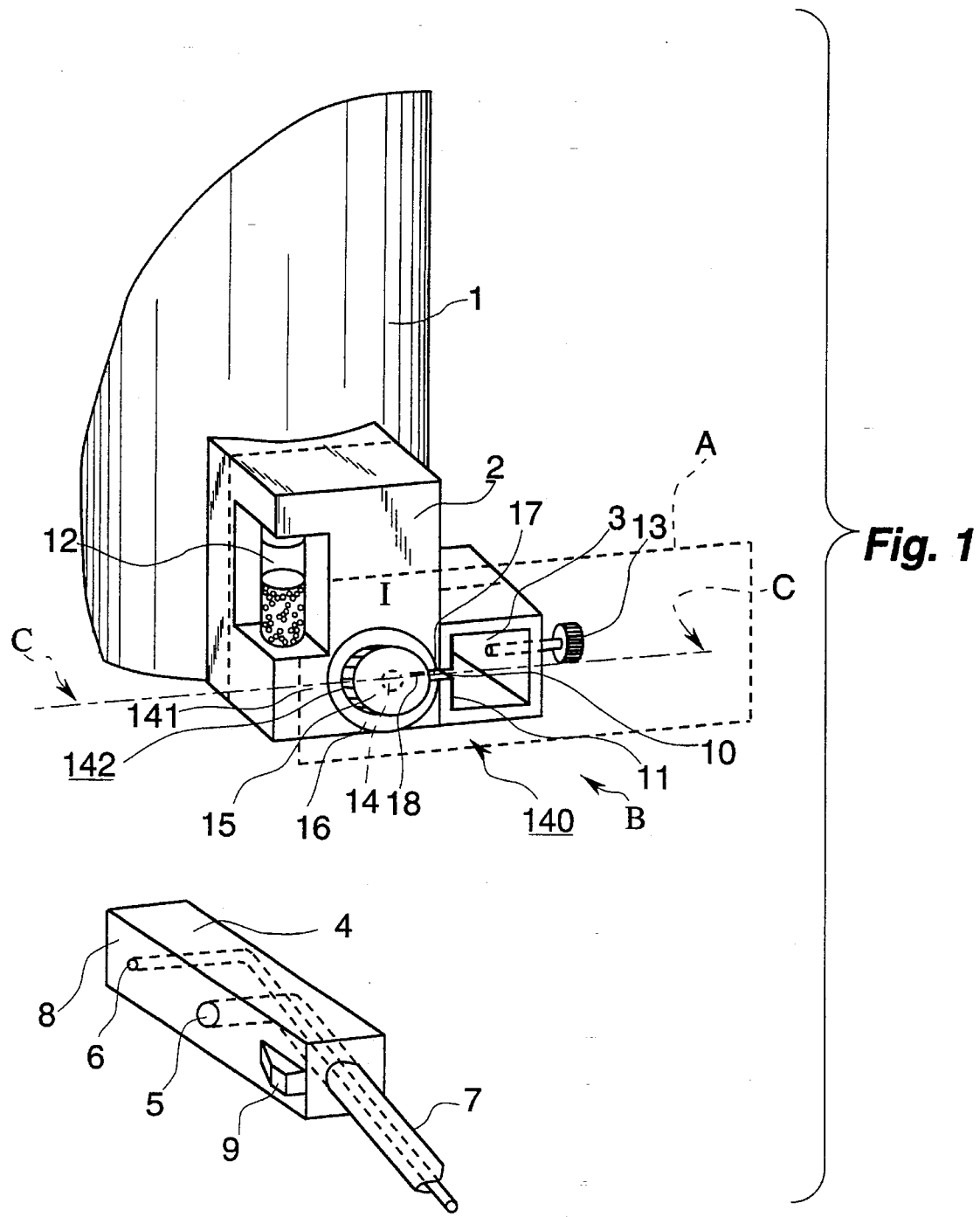
FIG. 1 is a perspective view showing a safety filling device on an anesthetic evaporator and a filling adapter shown withdrawn from an insertion opening in the device.

FIG. 1 shows a partial view of an anesthetic evaporator 1 with a safety filling device 2, which has an insertion opening 3 for connecting a filling adapter 4. The filling adapter 4 has a filling channel 5 and a ventilation channel 6, which are continued in a flexible line section 7 and open into a storage bottle, not shown in FIG. 1. The filling and ventilation channels 5, 6 are arranged at a sealing surface 8 of the filling adapter 4, and a cam-like projection 9, which can be pushed into a coding groove 10 of a corresponding design in the insertion opening 3, is additionally arranged at the sealing surface 8. The sealing surface 8 of the filling adapter is pressed against a seal 11 on the insertion opening 3 within the insertion opening 3, as a result of which the filling channel 5 and the ventilation channel 6 of the filling adapter 4 are sealingly in connection with the corresponding channels 5, 6 within the safety filling device 2, which is, however, not shown in FIG. 1. The channels 5, 6 within the safety filling device 2 lead to a filling space, likewise not shown in FIG. 1, whose degree of filling can be read from an inspection glass 12.

A closing element 140, which consists of a housing 141 with a movable control element 142, is arranged within the path of the device-side ventilation channel 6. The control element 142 includes a valve shaft 14 and a pushbutton 15 with a coding disk 16, which pushbutton actuates the valve shaft 14, and a shut-off valve, which is not shown in the figure, is actuated by the valve shaft 14 of the control element 142. The coding disk 16 has a recess 17 designed correspondingly to the coding groove 10. The shut-off valve opens or closes the ventilation channel 6 within the safety filling device 2.

To indicate the switching position of the closing element 140, a marking 18, which extends horizontally in FIG. 1 and indicates the switched-off position of the closing element 140 and of the shut-off valve, is provided on the pushbutton 15. The marking is directed toward the symbol "I" on the safety filling device 2 in the open position of the shut-off valve. In the switched-off position shown in FIG. 1, the recess 17 covers the coding groove 10, so that the filling adapter 4 with the projection 9 can be pushed into the insertion opening 3. If the pushbutton 15 is turned into position "I," the coding disk 16 covers the coding groove 10, so that the filling adapter 4 within the insertion opening 3 is blocked.

Figure 2:
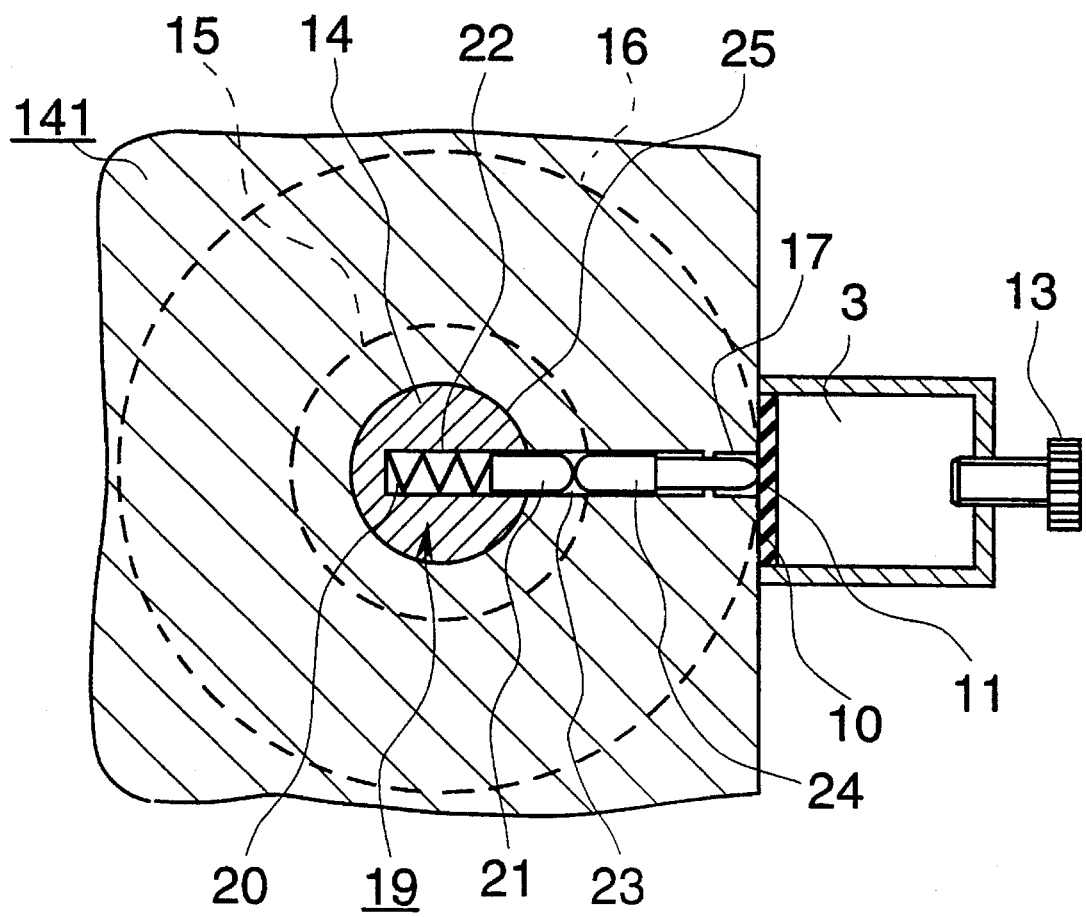
FIG. 2 is a longitudinal section of a detail A of the safety filling device according to FIG. 1 in the direction of view arrow B.

FIG. 2 shows a longitudinal section of detail A from FIG. 1, in the direction of view B toward the pushbutton 15. The outer contours of the pushbutton 15 and of the coding disk 16 are illustrated by broken lines in FIG. 2. Identical components are designated by the same reference numerals as in FIG. 1. The valve shaft 14, rotatably mounted in the housing 141, has a follower 19, which includes a spring 20, a locking pin 21, a guide hole 22 accommodating the locking pin 21 and the spring 20, and of a stop hole 23 opening into the coding groove 10 at a boundary line 25. The valve shaft 14 is located in a position which corresponds to the switched-off position of the closing element 140, and the locking pin 21 extends into the stop hole 23 from the guide hole 22 and over the boundary line 25, blocking the valve shaft 14 as part of the control element 142 within the housing 141 as a result. A transmission pin 24, which touches the locking pin 21, on the one hand, and ends within the coding groove 10, on the other hand, is also located in the stop hole 23. The coding groove 10 is covered flush by the recess 17 of the coding disk 16.

Figure 3:
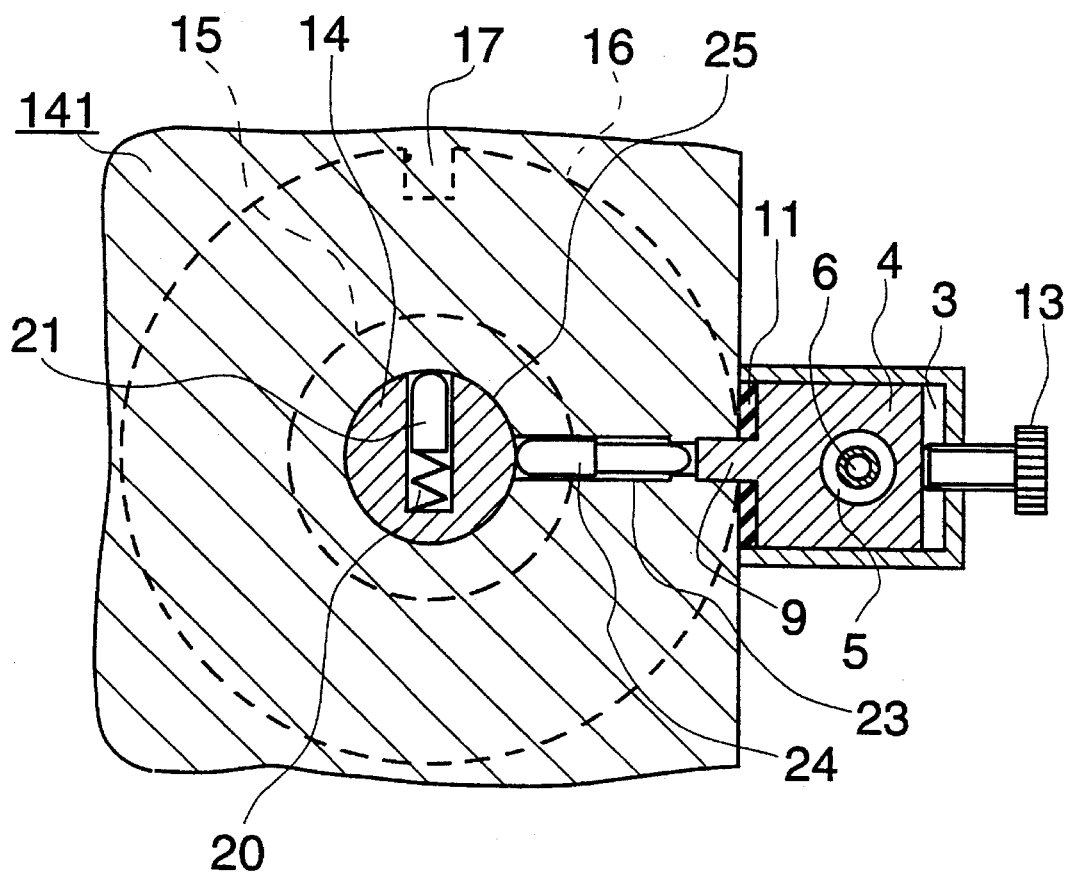

FIG. 3 shows detail A according to FIG. 2 in the case in which the filling adapter 4 has been pushed into the insertion opening 3. The transmission pin 24 is displaced by the projection 9 such that the locking pin 21 terminates flush with the boundary line 25 between the housing 141 and the valve shaft 14, so that the closing element 140, FIG. 1, can be brought into the open position via the valve shaft 14 and the pushbutton 15. This operating position is illustrated in FIG. 3, but the recess 17 is offset by 90° compared with the position according to FIG. 2. The projection 9 and consequently the filling adapter 4 within the insertion opening 3 are blocked by the coding disk 16, which covers the coding groove 10.

Figure 4:
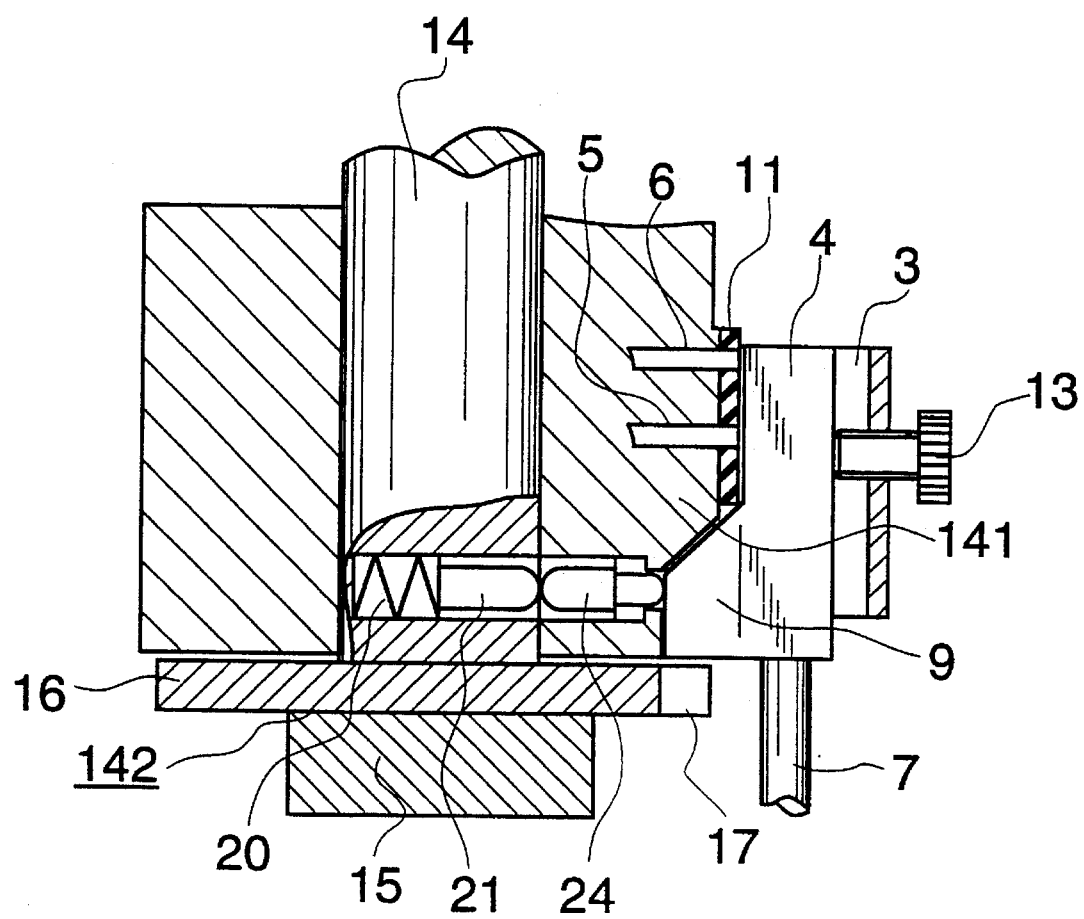
FIG. 4 is a sectional view C—C according to FIG. 1.

FIG. 4 shows the sectional view C—C according to FIG. 1, with the filling adapter 4 pushed into the insertion opening 3 and with the position of the pushbutton 15 as shown in FIG. 1.

Identical components are designated by the same reference numerals as in FIGS. 1 through 3. The filling channel 5 and the ventilation channel 6 are represented partially within the housing 141.

Figure 5:
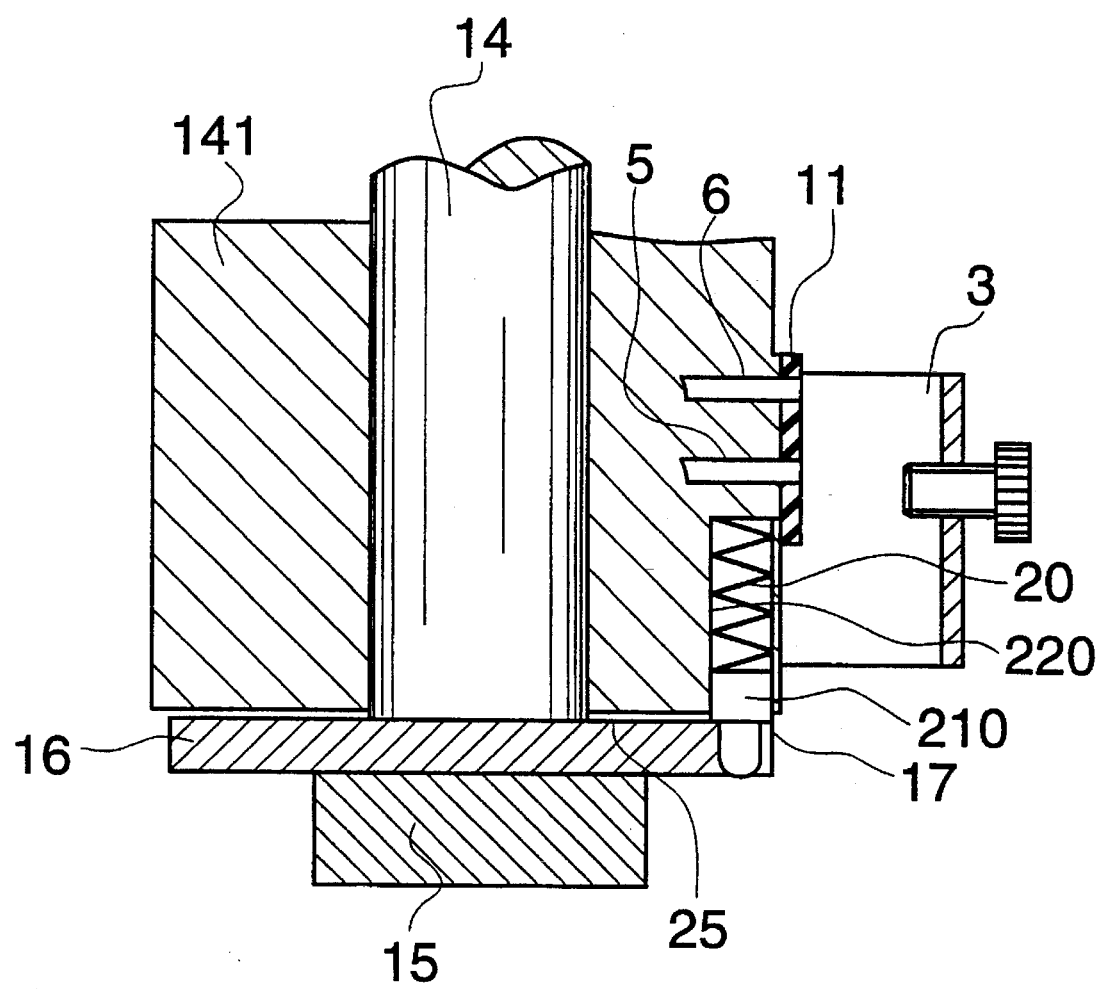
FIG. 5 is a sectional view showing an alternative design of a follower in the view according to FIG. 4.

FIG. 5 shows an alternative embodiment of a closing element blocked in the switched-off position in the view according to FIG. 4. The difference from FIG. 4 is that the guide hole is mounted as a first guide hole 220 in the housing 141, and the stop hole is a the recess 17 in the coding disk 16, while the recess 17 lies aligned on the first guide hole 220 in the switched-off position of the closing element 140, so that a first locking pin 210, which is located in the first guide hole 220 and is pretensioned with the spring 20, engages the recess 17 and thus blocks the coding disk 16. Identical components are designated by the same reference numerals as in FIGS. 1 through 4.

Figure 6:
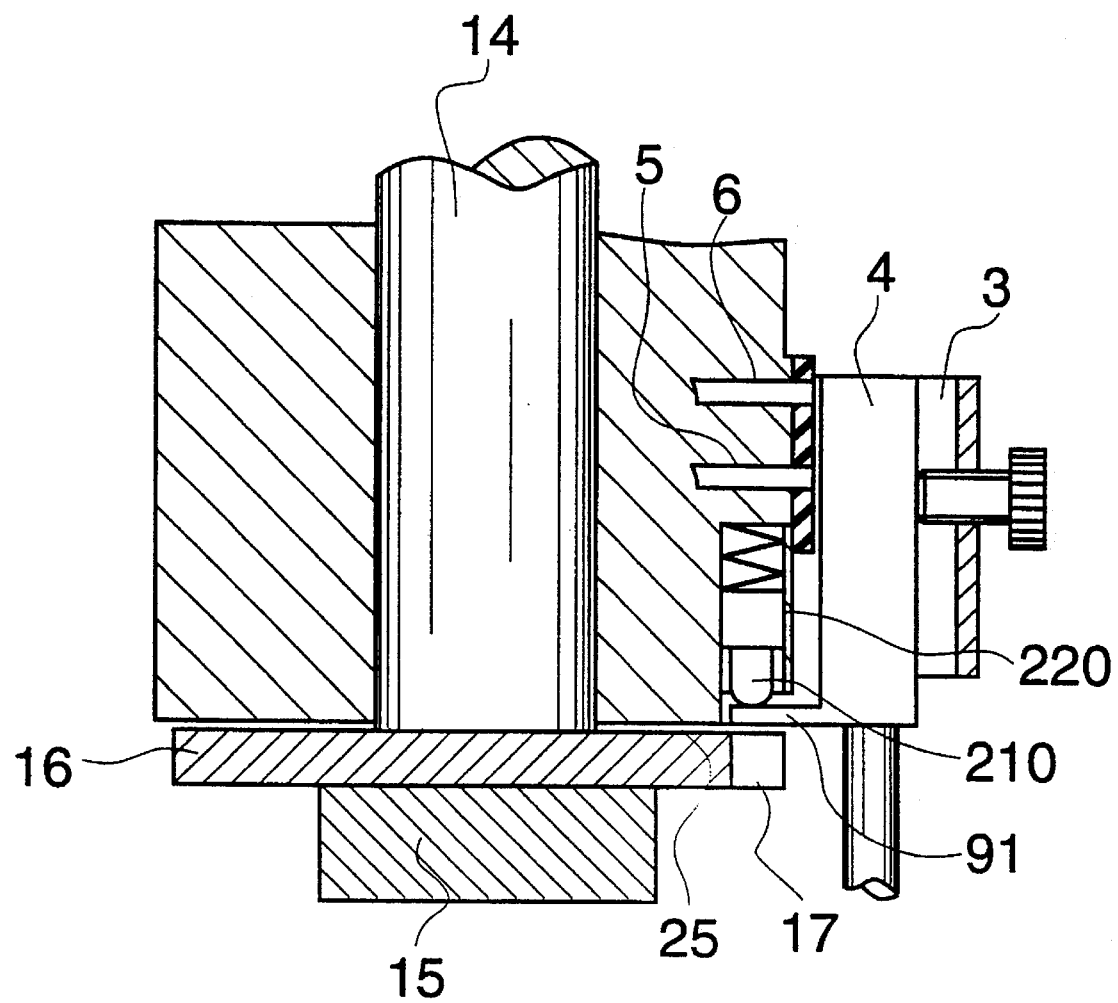

FIG. 6 illustrates the alternative design according to FIG. 5, but with the filling adapter 4 pushed in. The filling adapter 4 has a first projection 91, which has a more pin-like design here compared with the projection 9 according to FIG. 4, and it displaces the first locking pin 210 via the recess 17 over the boundary line 25 and into the first guide hole 220, so that the coding disk 16 is released, and the valve shaft 14 can be actuated by means of the pushbutton 15.

Figure 7:
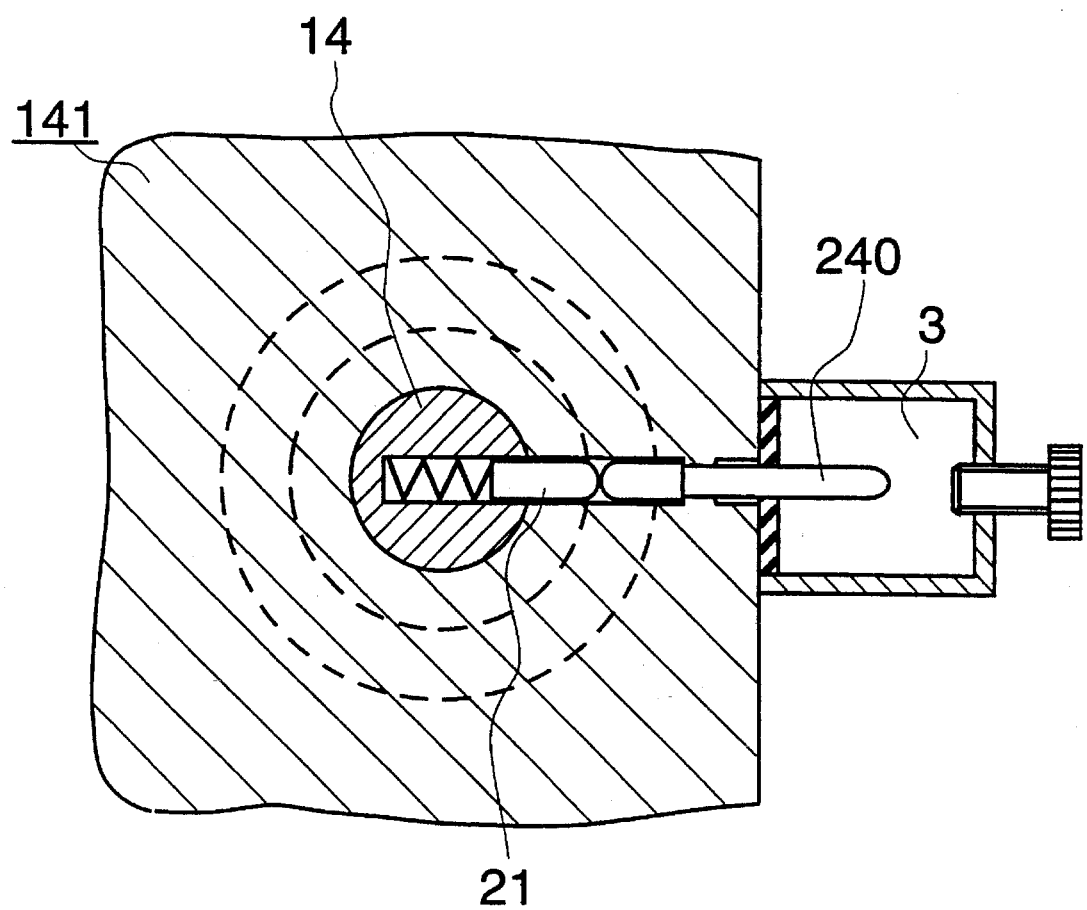
FIG. 7 is a sectional view showing another embodiment of a follower in the view according to FIG. 2.
Figure 8:
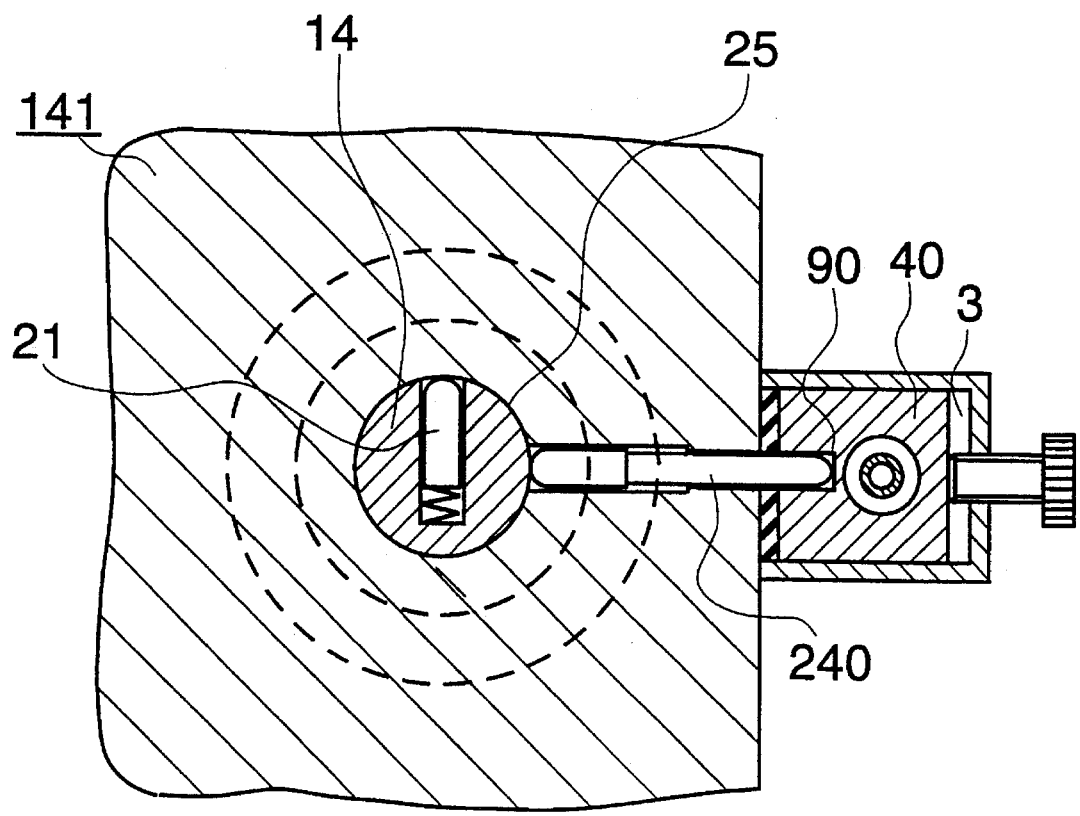

FIGS. 7 and 8 show—in the view according to FIGS. 2 and 3—another embodiment for a closing element blocked in the switched-off position. The difference from the design according to FIGS. 2 and 3 is the fact that the filling adapter is designed as a first filling adapter 40 with a depression 90 instead of a projection, and a first transmission pin 240 is provided instead of the transmission pin, and the first transmission pin 240 scans the depression 90 of the first filling adapter 40, and when the first filling adapter 40 has been pushed into the insertion opening 3, it displaces the locking pin 21 up to the boundary line 25, so that the valve shaft 14 can be actuated.

Figure 9:
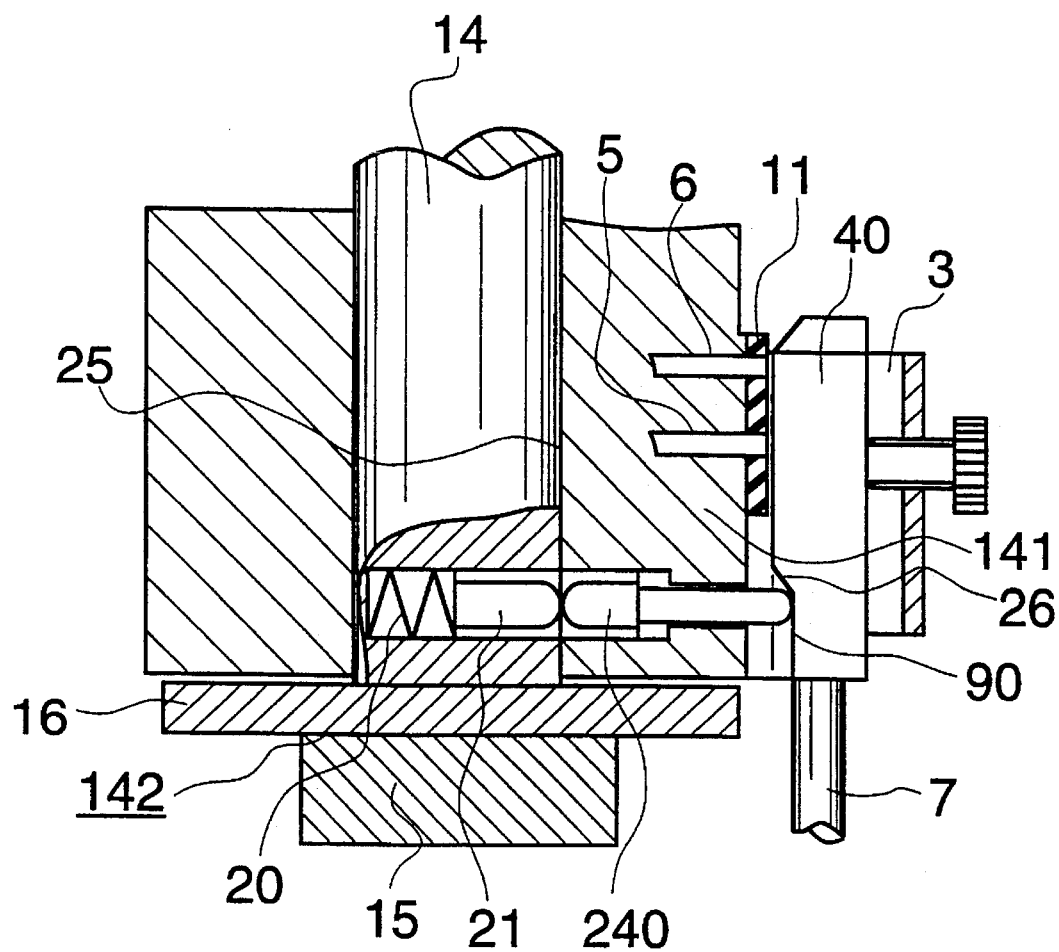
FIG. 9 is a sectional view of the follower according to FIG. 8 in the sectional view C—C according to FIG. 1.

FIG. 9 shows the embodiment according to FIG. 8 in the sectional view C—C according to FIG. 1. The depression 90 of the first filling adapter 40 is designed as a stepped depression with a step 26, which, viewed from the flexible line section 7, is located at a short distance behind the first transmission pin 240. The position of the control element 142 shown corresponds to the switched-off position of the closing element, in which the locking pin 21 and the first transmission pin 240 engage each other, and, due to the displaceability of the first transmission pin 240, the first filling adapter 40 can be pulled out and it can also be pushed into the insertion opening. If the control element 142 is actuated with the first filling adapter 40 pushed in, the locking pin 21 and the first transmission pin 240 will leave their overlapped position, as is illustrated, e.g., in FIG. 8, and the first filling adapter 40 is blocked in the insertion opening 3 by the first transmission pin 240, which is in contact with the step 26.

While specific embodiments of the invention have been shown and described in detail to illustrate the application of the principles of the invention, it will be understood that the invention may be embodied otherwise without departing from such principles.

What is claimed is:

1. Anesthetic evaporator safety filling device for filling liquid anesthetic into the anesthetic evaporator from a storage container, comprising:

a filling device housing, including means defining an insertion opening;

a filling adapter which can be pushed into said insertion opening, said filling adapter including a filling channel for delivering liquid anesthetic and a ventilation channel for compensating filling volume in the storage container, which filling volume changes during filling, said ventilation and filling channel extending out of said filling adapter;

closing means including a closing element for interrupting flow of liquid anesthetic in a switched-off position, said closing element means including a control element movable in said housing for setting a switching state, said closing element including a follower blocking said switched-off position, said follower being disposed between said housing and said control element; and a coding part engaging said follower in an operating position of said filling adapter, said coding part eliminating blockage of said closing element in said operating position of said filling adapter, said coding part being provided on said filling adapter.

2. Safety filling device according to claim 1, wherein said follower is formed of a guide hole in said control element, a stop hole in said housing, pointing toward said coding part, and a locking pin, which is displaceable in said guide hole and/or in said stop hole;

said guide hole and said stop hole passing over into each other at a boundary line in said switched-off position of said closing element;

said locking pin being displaceable by said coding part at least up to said boundary line in said switched-off position.

3. Safety filling device according to claim 1, wherein said follower is formed of a first guide hole in said housing, a first stop hole in said control element, which stop hole points toward said coding part, and a first locking pin, which is displaceable in said first guide hole and/or displaceable in said first stop hole;

said first guide hole and said first stop hole passing over into one another at a boundary line in said switched-off position of said closing element; and a first locking pin displaceable by said coding part at least up to boundary line in said switched-off position.

4. Safety filling device according to claim 1, wherein said coding part is formed as a projection.

5. Safety filling device according to claim 4, wherein said insertion opening is provided with a coding groove, into which said projection can be pushed.

6. Safety filling device according to claim 2, wherein said control element has a pushbutton with a coding disk and said first stop hole is designed as a recess in said coding disk.

7. Safety filling device according to claim 6, wherein said recess is designed to correspond to said coding groove and said recess lies overlappingly on said coding groove in said switched-off position of said closing element.

8. Safety filling device according to claim 3, wherein said control element has a pushbutton with a coding disk and said first stop hole is designed as a recess in said coding disk.

9. Safety filling device according to claim 1, wherein said coding part is designed as a depression in said filling adapter and a first transmission pin scanning said depression is provided between said locking pin and said filling adapter.

10. Safety filling device according to claim 9, wherein said depression is designed as a stepped depression with at least one step, which is in contact with said first transmission pin in said operating position of said filling adapter.

11. Safety filling device according to claim 8, wherein said recess is designed to correspond to said coding groove and said recess lies overlappingly on said coding groove in said switched-off position of said closing element.

* * * * *